(12) United States Patent
Polluks

(10) Patent No.: US 11,058,289 B2
(45) Date of Patent: Jul. 13, 2021

(54) VIDEOENDOSCOPE

(71) Applicant: Karl Storz SE & Co. KG, Tuttlingen (DE)

(72) Inventor: Indrek-Toomas Polluks, Laagri (EE)

(*) Notice: Subject to any disclaimer, the term of this patent is extended or adjusted under 35 U.S.C. 154(b) by 441 days.

(21) Appl. No.: 16/041,301

(22) Filed: Jul. 20, 2018

(65) Prior Publication Data

US 2019/0029506 A1    Jan. 31, 2019

(30) Foreign Application Priority Data

Jul. 25, 2017    (DE) .................. 102017116827.3

(51) Int. Cl.
| | |
|---|---|
| *A61B 1/05* | (2006.01) |
| *A61B 1/045* | (2006.01) |
| *A61B 1/00* | (2006.01) |
| *G02B 23/24* | (2006.01) |
| *A61B 1/005* | (2006.01) |

(52) U.S. Cl.
CPC ............ *A61B 1/051* (2013.01); *A61B 1/0008* (2013.01); *A61B 1/0011* (2013.01); *A61B 1/0057* (2013.01); *A61B 1/00124* (2013.01); *A61B 1/045* (2013.01); *G02B 23/2484* (2013.01)

(58) Field of Classification Search
CPC ...... A61B 1/051; A61B 1/0008; A61B 1/0011
USPC ...................................................... 600/134
See application file for complete search history.

(56) References Cited

U.S. PATENT DOCUMENTS

| | | | |
|---|---|---|---|
| 5,868,664 A | 2/1999 | Speier et al. | |
| 5,873,816 A | 2/1999 | Kagawa et al. | |
| 6,547,721 B1* | 4/2003 | Higuma | A61B 1/051 |
| | | | 600/133 |
| 2010/0261961 A1 | 10/2010 | Scott et al. | |
| 2014/0166493 A1* | 6/2014 | Dingeldein | C25D 11/005 |
| | | | 205/106 |

FOREIGN PATENT DOCUMENTS

| | | |
|---|---|---|
| DE | 102009023459 A1 | 12/2010 |
| WO | 2010139451 A2 | 12/2010 |
| WO | 2016064763 A1 | 4/2016 |

* cited by examiner

*Primary Examiner* — Matthew J Kasztejna
(74) *Attorney, Agent, or Firm* — Michael Joseph Loi; David Noel Villalpando

(57) ABSTRACT

Video endoscope comprising a distal end with a video camera assembly and a lens assembly arranged along a longitudinal axis, the video camera assembly comprising a video module, a video module holder, a proximal bushing arranged on the video module holder, a metal shield enclosing the video module along the longitudinal axis, and a flexible video cable, wherein the video cable is connected to the video module, runs through the video module holder and the proximal bushing away from the video module and is in contact with the bushing, wherein the video module comprises a video imager and control circuitry, wherein the metal shield has on its outside a dielectric coating obtained by material treatment of the metal shield, and wherein a maximum cross section of the distal end is less than 0.75 $cm^2$. Further, a video endoscopy system is disclosed.

20 Claims, 5 Drawing Sheets

VIDEOENDOSCOPE

CROSS REFERENCES TO RELATED APPLICATIONS

This application claims priority from German patent application 10 2017 116 827.6, filed on Jul. 25, 2017. The entire contents of this priority application is incorporated herein by reference.

BACKGROUND OF THE DISCLOSURE

The present disclosure relates to a video endoscope and a video endoscopy system.

The range of surgeries that are performed as minimally-invasive surgeries using endoscopic instruments, e.g. endoscopes, is continuously increasing. The effects of a reduced trauma to a patient and the reduced time for a patient's recovery must be considered as notable improvements over classical, i.e. invasive surgery techniques. However, minimally-invasive surgery also introduces new challenges.

On the one hand, surgeons have to learn and obtain sufficient practical experience when performing a surgery only through one or more small openings in the patient's body. Since the entry point into the patient's body essentially defines a pivot point for the endoscope, surgeons must get acquainted with new ways on how to use medical instruments in order to manipulate tissue inside the patient's body.

On the other hand, a significant challenge remains in that the surgeon cannot view the surgical site in a direct line of sight. Rather, since the endoscope is introduced through a small opening, the surgical site is typically completely hidden from the surgeon. Therefore, a video endoscope is required that allows the surgeon to view the surgical site on a monitor. While present video endoscopes render high-quality images, inserting the video endoscope into the patient's body can still cause trauma to the patient.

For some surgeries this trauma may be considered negligible, e.g. when performing a laparoscopic surgery in the abdomen through the abdominal wall. However, other parts of the body are very sensitive to any additional trauma caused by the introduction of a video endoscope, e.g. the airways or the urethra and ureters when performing surgery in the bladder or the kidneys, or any other natural orifice of small diameter.

Therefore, even today there remains the challenge that endoscopes must become smaller, i.e. in view of their cross section that is inserted into the patient's body. Especially when the maximum cross section of the distal end of the endoscope has to be less than 0.75 cm$^2$, less than 0.5 cm$^2$, less than 0.25 cm$^2$ or even less than 0.15 cm$^2$, it is still a challenge today to produce video endoscopes with this size and including all necessary components, such as video sensor, illumination, deflection and working channel.

SUMMARY OF THE DISCLOSURE

In view of the above it is one object to disclose a video endoscope and a corresponding video endoscopy system with a distal end having a small maximum cross section which can be produced efficiently.

According to one aspect of the present disclosure there is provided a video endoscope comprising a distal end with a video camera assembly and a lens assembly arranged along a longitudinal axis, the video camera assembly comprising a video module, a video module holder, a proximal bushing arranged on the video module holder, a metal shield enclosing the video module along the longitudinal axis, and a flexible video cable, wherein the video cable is connected to the video module, runs through the video module holder and the proximal bushing away from the video module and is in contact with the bushing, wherein the video module comprises a video imager and control circuitry, wherein the metal shield has on its outside a dielectric coating obtained by material treatment of the metal shield, and wherein a maximum cross section of the distal end is less than 0.75 cm$^2$.

The general functionality of a video endoscope is known, so that it will be described here only briefly. The distal end of the video endoscope is inserted into a patient's body and is directed at a surgical site which is typically illuminated by a light source on the distal end. Light from the surgical site enters the video endoscope via the lens assembly through which it is forwarded to the video imager of the video module. The video imager may be of any suitable type, including known CCD or CMOS image sensors. The information from the video imager is processed by the control circuitry, and the resulting data is sent via the flexible video cable to a receiving element which is typically a camera control unit.

The dielectric coating provides an electric insulation. Since the coating can be chosen to be less than 100 µm or even less than 50 µm, the coating has only a negligible effect on the overall maximum cross section of the distal end. Because the dielectric coating is obtained by material treatment of the metal shield, the outer insulation required for the metal shield can be provided at a very small thickness. In particular, the dielectric coating is notably thinner than the known plastic enclosures or heat-shrink tubes, so that in comparison to the prior art a reduction of the cross section of the distal end can be achieved.

It is noted that, according to some exemplary embodiments, the dielectric coating is applied at least over the full outer surface of the metal shield. However, for some exemplary embodiments, the dielectric coating may be applied at least to parts of the inside of the metal shield. For some exemplary embodiments the whole metal shield may be provided with the dielectric coating. For some exemplary embodiments the maximum cross section of the distal end is less than one of 0.5 cm$^2$, 0.25 cm$^2$ and 0.15 cm$^2$.

According to an exemplary embodiment, the material treatment comprises or is constituted by one of oxidation, plasma electrolytic oxidation and micro arc oxidation.

These methods of material treatment allow to achieve the insulating function at a small thickness. Also, a coating obtained by these methods can be considered very robust and suited for long-term use.

According to a further exemplary embodiment the metal shield is predominantly made of one of aluminum, magnesium and titanium.

These materials are well-suited for a video endoscope and produce good results when subjected to the material treatments indicated above. It is noted that the term "predominantly" indicates that the metal shield comprises a high amount of the respective material. This includes that the metal shield is made completely of aluminum, magnesium or titanium.

According to a further exemplary embodiment the metal shield is not covered by a heat-shrink tube or not covered by any plastic insulator at all.

It is noted that the proposed dielectric coating is sufficient for the required insulation purposes. Therefore, in order to keep the total cross section of the distal end low, the typical heat-shrink tube is omitted or there is no plastic insulator on the outside of the metal shield. In particular, the thickness of the dielectric coating is less than the thickness of a heat-shrink tube.

According to a further exemplary embodiment the metal shield has a first section with a first, at least substantially rectangular cross section, and a second section with a second, at least substantially oval cross section. For another exemplary embodiment an intermediate section is provided that transitions the first cross section into the second cross section along the longitudinal axis.

The first, rectangular cross section, which, for an exemplary embodiment, may have a square shape, allows for extra room within the metal shield. This means that elements of the video camera assembly can extend more in a direction perpendicular to the longitudinal axis instead of a direction along the longitudinal axis. This means that the video camera assembly can become shorter along the longitudinal axis thus making the distal end of the video endoscope more compact along the longitudinal axis. This may improve the maneuverability of the distal end for flexible or bendable endoscopes. The second section, which, for an exemplary embodiment, may have a circular cross section, allows to reduce the cross section down to what is needed to run the flexible video cable away from the video camera assembly and out of the bushing and the metal shield. For an exemplary embodiment, there is an intermediate section that allows for a smooth transition between the first cross section and the second cross section along the longitudinal axis.

According to a further exemplary embodiment, the metal shield has on its inside a contact area where the dielectric coating is not applied, and, for another exemplary embodiment, the contact area may be in contact with the bushing.

Leaving a contact area inside the metal shield void of the dielectric coating, for example by masking the contact area during the material treatment, may help to establish an electrical contact with the metal shield, e.g. in order to ground the metal shield. When the contact area is in contact with the bushing, the metal shield may be tightly seated on the bushing. Further, the contact area may be used to establish an electrical contact to the bushing. Then, if, as for some exemplary embodiments, the bushing is grounded, the metal shield is grounded as well.

According to a further exemplary embodiment, a largest cross section of the metal shield viewed perpendicular to the longitudinal axis has the shape of a square with rounded corners.

This embodiment allows to strike a good compromise between making room available within the metal shield while ensuring that there are no acute edges. When looking at the cross section of the metal shield its perimeter comprises four rounded corners that are distinct from the straight lines forming the square. Looking at a ratio of the length of the rounded corners along the perimeter in relation to the total perimeter, the ratio may be, for some exemplary embodiments, between one of 1% and 30%, 5% and 25%, and 10% and 20%.

According to a further exemplary embodiment the video cable has a conductive shield that is electrically connected to the bushing, which, for another exemplary embodiment, may be provided by using a solidified conductive adhesive.

This embodiment simplifies a grounding of the bushing by connecting the grounded conductive shield of the video cable with the bushing. For some exemplary embodiments, the electrical contact is achieved or improved using a solidified conductive adhesive. The adhesive may be inserted in its liquid form to ensure that a good contact area between the conductive shield of the video cable and the bushing is achieved. The adhesive later solidifies so that a robust electrical connection is achieved.

According to a further exemplary embodiment the bushing has a clearance directed perpendicular to the longitudinal axis allowing to reach the video cable inside the bushing.

The clearance allows to introduce a liquid or pasty adhesive directly to the mechanical contact area between the video cable and the bushing, so that a good electrical connection between the video cable and the bushing can be achieved as explained before.

According to a further exemplary embodiment, the bushing has at its proximal end a fixing area where the bushing is in contact with the video cable, the fixing area comprising at least one slit that allows the fixing area to be compressed and to be pressed onto the video cable.

During production, the video cable is fed through the fixing area. Then, applying pressure to the fixing area, the fixing area is compressed and thus pressed onto the video cable. When doing so, the at least one slit will become closed or at least partially closed. Assuming that the fixing area has an annular shape where the longitudinal axis represents the normal vector of the resulting area, the fixing area has, for some exemplary embodiments, one slit at 0° of the annulus and another slit at 180°. Further slits can be provided as needed. After the annular fixing area has been compressed, its cross section may resemble an oval.

According to a further exemplary embodiment the bushing has at its proximal end an opening with a center that is offset in a direction perpendicular to the longitudinal axis from a center of the video imager.

This allows for extra room inside the endoscope shaft in order to run a further element to the distal end of the metal shield. For example, a pull wire may be attached to the distal end of the video endoscope in order to manipulate a deflection of the distal end.

According to a further exemplary embodiment the bushing has a deformable rib that deforms towards the inside of the bushing when pushed in a direction perpendicular to the longitudinal axis, wherein the video module holder has a recess at a position corresponding to the rib, so that the rib can be pushed at least partially into the recess thus fixing the bushing relative to the video module holder regarding at least one of a movement in a direction of the longitudinal axis and a rotation around the longitudinal axis.

This embodiment may help to simplify the production process of the video endoscope. For some exemplary embodiments, the rib has two mechanical connection points to the bushing with a free extension between these two points. For some exemplary embodiments, when the rib is pushed towards the inside, the rib stays connected to the bushing at both points. For other exemplary embodiments, the rib extends on a roughly circular path around the longitudinal axis, and a circular arc of the circular path is between one of 20° and 120°, 30° and 90°, 40° and 60°.

According to a further exemplary embodiment the bushing is made out of a conductive material and/or the video module holder is made of a plastic material.

The bushing being made of a conductive material allows for a good grounding and shielding by at least one of the bushing and the electrically connected metal shield. The video module holder being of a plastic material allows for an easy insulation of the video module and its video imager and control circuitry.

According to a further exemplary embodiment the bushing is electrically connected to the metal shield by a solidified conductive adhesive.

This embodiment allows for a good and durable electric connection between the bushing and the metal shield.

According to a further aspect there is disclosed a video endoscopy system comprising a video endoscope, as explained above, and further comprising a handle, a pull wire and a camera control unit, wherein a first end of the pull wire is attached to the distal end of the video endoscope and a second end of the pull wire is attached to a control element on the handle, so that by manipulating the control element a user can adjust a deflection of the distal end, and wherein the video cable is connected to the camera control unit.

It is noted that the previously indicated features and the features that will be explained in the following cannot only be provided in the explicitly disclosed combination but also in other combinations or even in isolation without departing from the scope of and spirit of the present disclosure.

BRIEF DESCRIPTION OF THE DRAWINGS

Embodiments are disclosed in the drawings and are explained in the following description. In the figures.

DESCRIPTION OF EXEMPLARY EMBODIMENTS

Figure 1:
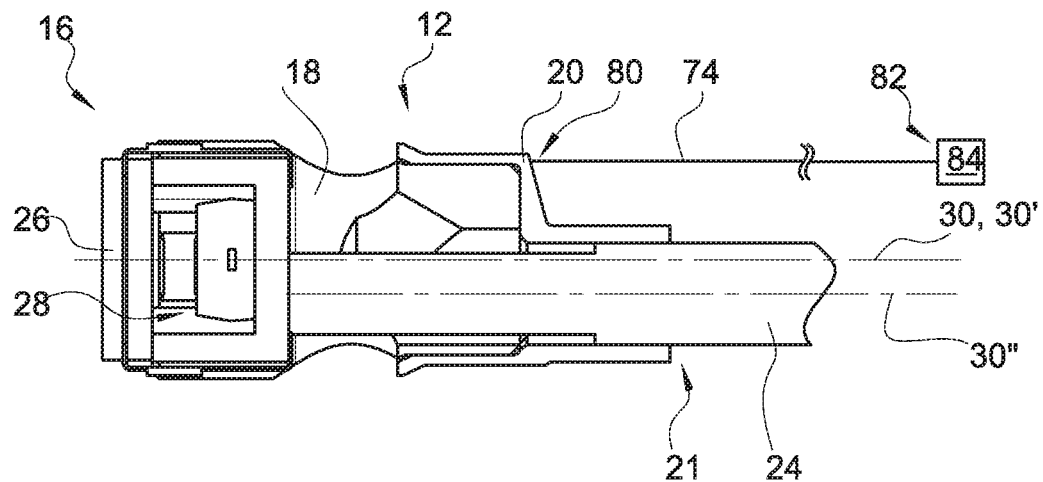
FIG. 1 shows a cross section through the inner parts of a video module assembly according to an exemplary embodiment.
Figure 3:
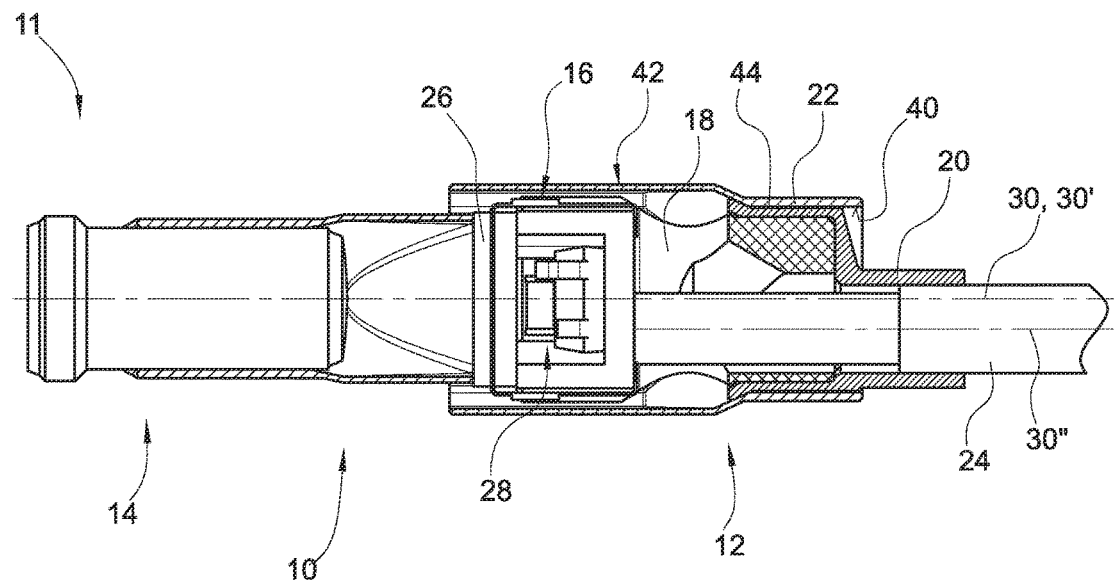
FIG. 3 shows a side view as a partial cross section of a video endoscope according to an exemplary embodiment.

FIG. 1 shows the inner parts of a video camera assembly 12 of a video endoscope 10 (see FIG. 3). The video camera assembly 12 comprises a video module 16, a video module holder 18, a proximal bushing 20 arranged on the video module holder 18 and a flexible video cable 24 that is connected to the video module 16. The video cable 24 further runs through the video module holder 18 and the proximal bushing 20 away from the video module 16 and is in contact with the bushing 20. For this purpose, both the video module holder 18 and the bushing 20 have an opening. The video camera assembly 12 further comprises a metal shield 22 (see FIG. 3).

The video module 16 comprises a video imager 26 and corresponding control circuitry 28. The metal shield 22 has on its outside a dielectric coating obtained by material treatment of the metal shield 22. A distal end 11 of the video endoscope 10 which comprises the video camera assembly 12 and the lens assembly 14 has a maximum cross section of less than $0.75 \text{ cm}^2$.

For orientation purposes, a longitudinal axis 30 is shown along which the video camera assembly 12 and the lens assembly 14 (see FIG. 3) are arranged. The longitudinal axis 30 is the same as a center imager longitudinal axis 30' of the video imager 26, the video module 16, and the video module holder 18. It is noted that the cable 24 extends substantially along the same longitudinal axis 30.

The bushing 20 has at its proximal end an opening 21 with a center, through which a center bushing longitudinal axis 30" passes, that is offset in a direction perpendicular to the longitudinal axis 30 from a center of the video imager 26, through which the center imager longitudinal axis 30' passes.

Also, as an optional feature, FIG. 1 shows a pull wire 74 which is attached with a first end 80 to the distal end 11 of the video endoscope 10, here to the bushing 20. A second end 82 of the pull wire 74 is attached to a control element 84 that allows to push or pull the pull wire 74 and thus adjust a deflection of the distal end 11. The pull wire 74 is typically guided in a sheath 76 (see FIG. 7).

Figure 2:
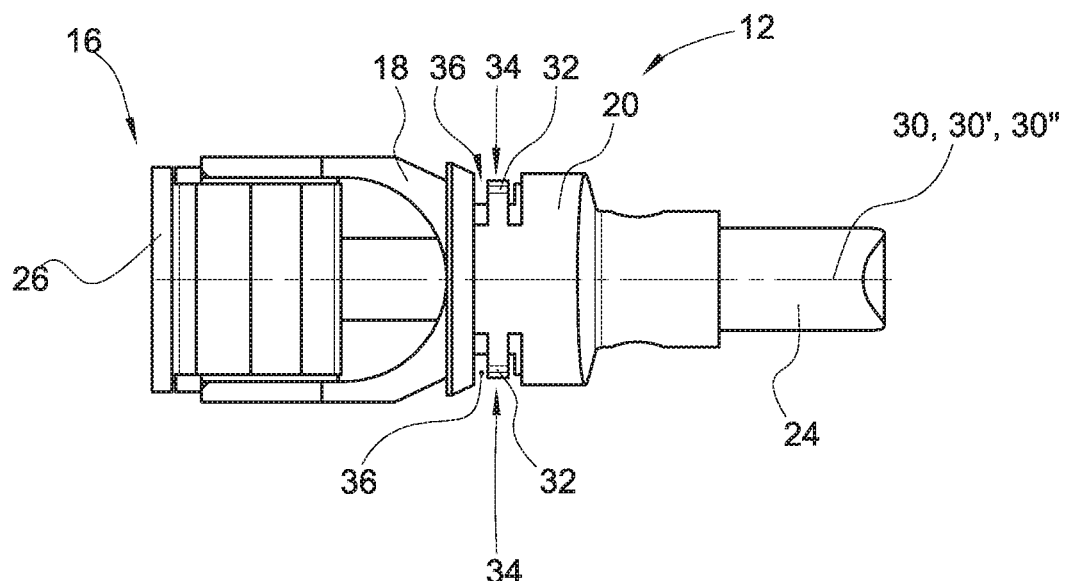
FIG. 2 shows a view from the top onto the inner parts of the video module assembly shown in FIG. 1.

FIG. 2 shows the inner parts of the video camera assembly 12 when viewed from the top. Here and in the following the previously introduced numbering of the individual elements will be maintained.

This view shows that the bushing 20 has two deformable ribs 32 that can be deformed towards the inside of the bushing 20 when pushed in a direction perpendicular to the longitudinal axis 30 as indicated by the arrows 34. The video module holder 18 has two recesses 36 at a position corresponding to the ribs 32, respectively. This allows to push the ribs 32 at least partially into the corresponding recess 36 thus fixing the bushing 20 relative to the video module holder 18. For some exemplary embodiments, the fixing ensures that the bushing 20 and the video module holder 18 do not rotate relative to each other around the longitudinal axis 30. At the same time, the fixing may be used to prevent a movement of these two elements relative to another in a direction of the longitudinal axis 30.

FIG. 3 shows the distal end 11 of the video endoscope. In comparison to the situation shown in FIG. 1, the lens assembly 14 is depicted distally to the video imager 26, and the inner parts of the video camera assembly 12 are surrounded by the metal shield 22.

The metal shield 22 has on its inside a contact area 40 where the dielectric coating 42 is not applied. The contact area 40 is in contact with the bushing 20. Thereby, an electrical connection between the metal shield 22 and the bushing 20 is obtained. The electrical connection is improved by a solidified conductive adhesive 44 between the contact area 40 and the bushing 20.

Figure 4:
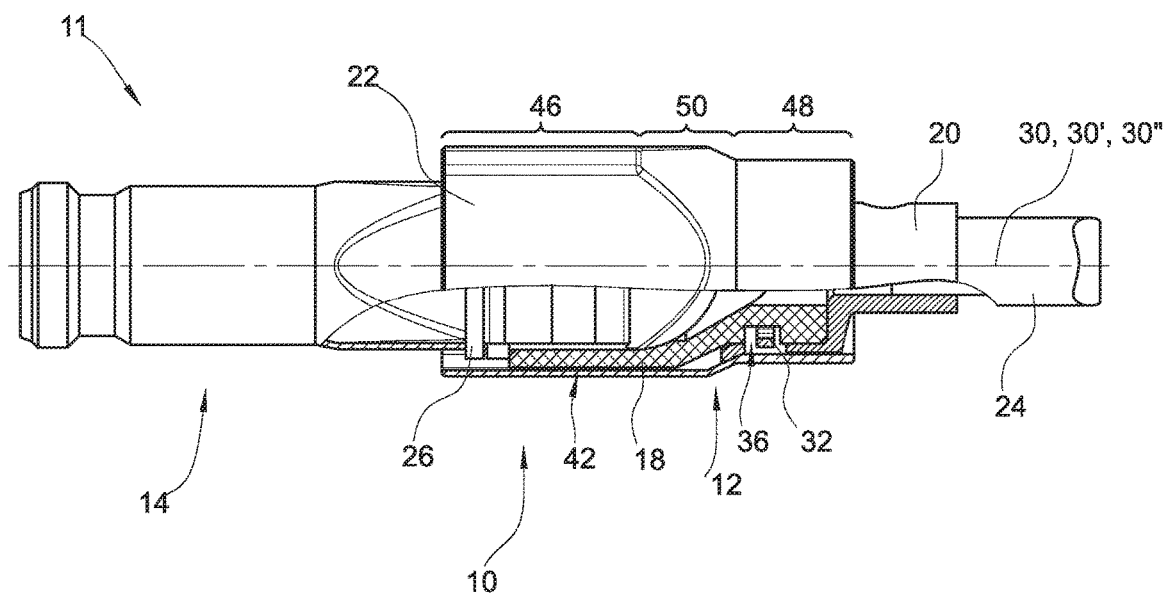
FIG. 4 shows a view from the top onto the video module of FIG. 3 with a cut-open portion including a partial cross section.

FIG. 4 shows the distal end 11 of FIG. 3 in a view from the top. The metal shield 22 has a first section 46 with a first, at least substantially rectangular cross section and a second section 48 with a second, at least substantially oval cross section. Further, an intermediate section 50 transitions the first cross section 46 into the second cross section 48 along the longitudinal axis 30.

Figure 5:
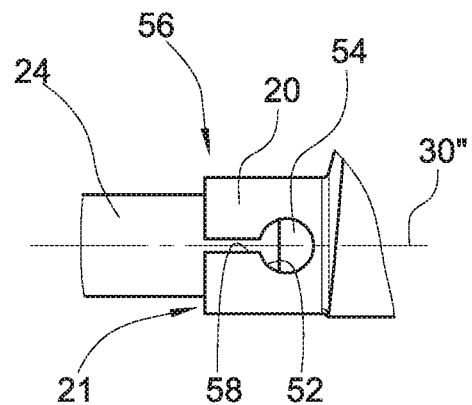
FIG. 5 shows a detail of the connection between the bushing and the video cable.

FIG. 5 shows a detail of the area where the cable 24 runs from the proximal end (on the left hand side of the figure) of the bushing 20 through the opening 21. The bushing 20 has two clearances 52, one of them is hidden on the other side in this view, that are directed perpendicularly to the longitudinal axis 30—and the center bushing longitudinal axis 30" since both longitudinal axes 30, 30" are parallel—providing access to the video cable 24 inside the bushing 20.

As can be seen through the clearance 52, the video cable 24 has a conductive shield 54. Access to the conductive shield 54 can be obtained, e.g., by partially removing an outer insulator of the cable 24. Since the video cable 24 can be reached through the clearance 52, it is possible to introduce a liquid or pasty conductive adhesive which solidifies and creates a good electrical connection between the conductive shield 54 and the bushing 20.

Further, it is shown that the bushing 20 has at its proximal end a fixing area 56 where the bushing 20 is in mechanical contact with the video cable 24. The fixing area 56 has two slits 58, one of the slits 58 in this view being hidden on the other side, that allow the fixing area 56 to be compressed and to be pressed onto the video cable 24 during assembly. The situation shown in FIG. 5 represents the situation when the fixing area 56 has not been compressed yet. When the fixing area 56 is compressed, the slits 58 will become at least partially closed. As an alternative, the fixing area 56 as shown in FIG. 5 may be spread open before it is pressed onto the video cable 24, so that after compressing the fixing area 56 onto the video cable 24, the situation shown in FIG. 5 is obtained.

Figure 6:
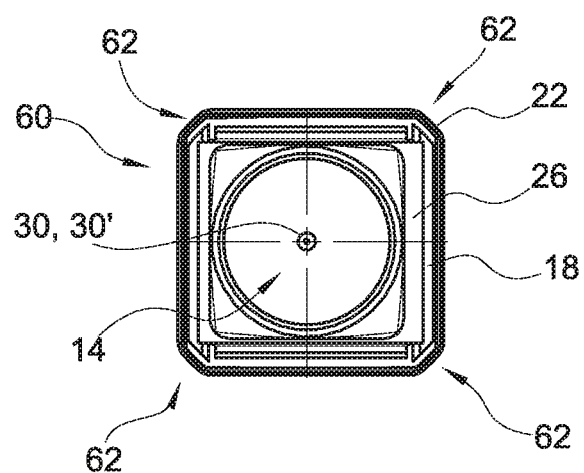
FIG. 6 shows a front view onto the video module of FIG. 3.

FIG. 6 shows a front view onto the distal end 11 of the camera assembly 12. It can be seen that a largest cross section of the metal shield 22, here viewed perpendicular to the longitudinal axis, has the shape of a square 60 with rounded corners 62.

Figure 7:
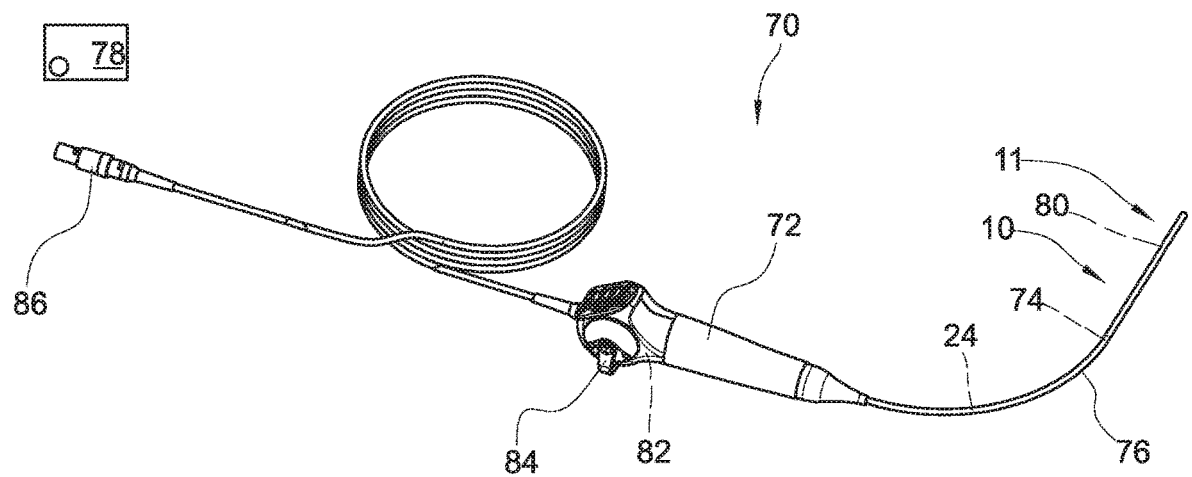
FIG. 7 shows a video endoscopy system according to an embodiment.

FIG. 7 shows a video endoscopy system 70 comprising a video endoscope 10, a handle 72, a pull wire 74 (hidden inside a sheath 76) and a camera control unit 78 to which the video endoscope 10 can be connected.

A first end 80 (hidden) of the pull wire 74 is attached to the distal end 11 of the video endoscope 10. A second end 82 (hidden) of the pull wire 74 is attached to a control element 84 on the handle 72. By manipulating the control element 84 a user can adjust a deflection of the distal end 11. The video cable 24 which is hidden by the sheath 76 can be connected to the camera control unit 78 via coupler 86.

Figure 8:
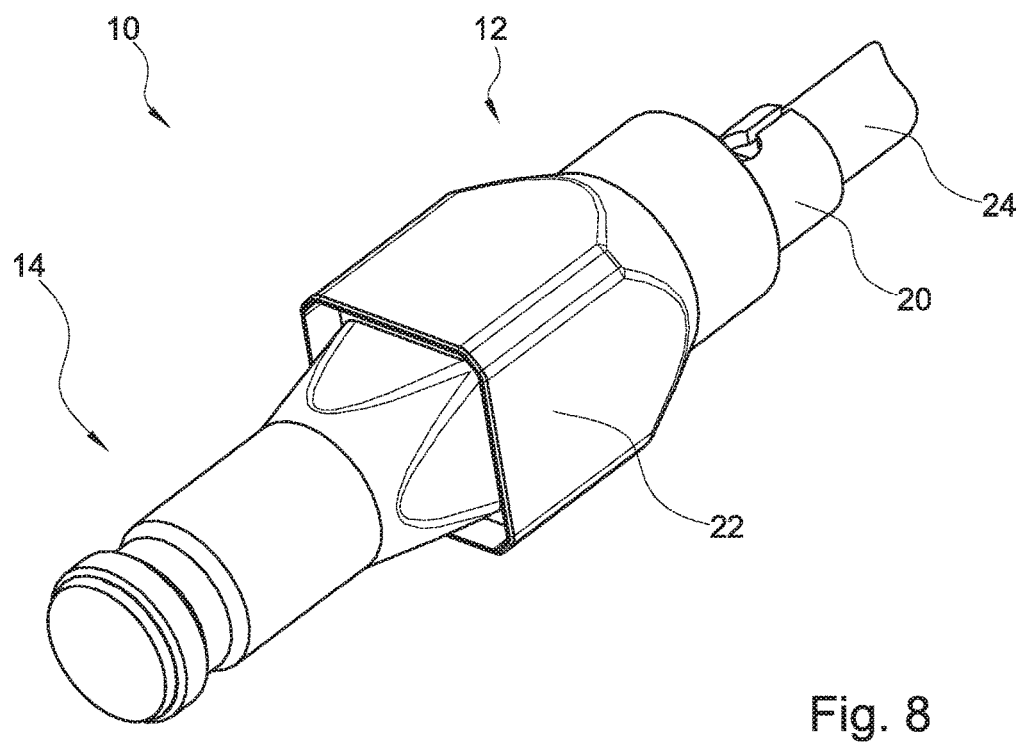
FIG. 8 shows a perspective view of the video endoscope shown in FIG. 3.

FIG. 8 discloses a perspective view of the video endoscope 10.

Figure 9:
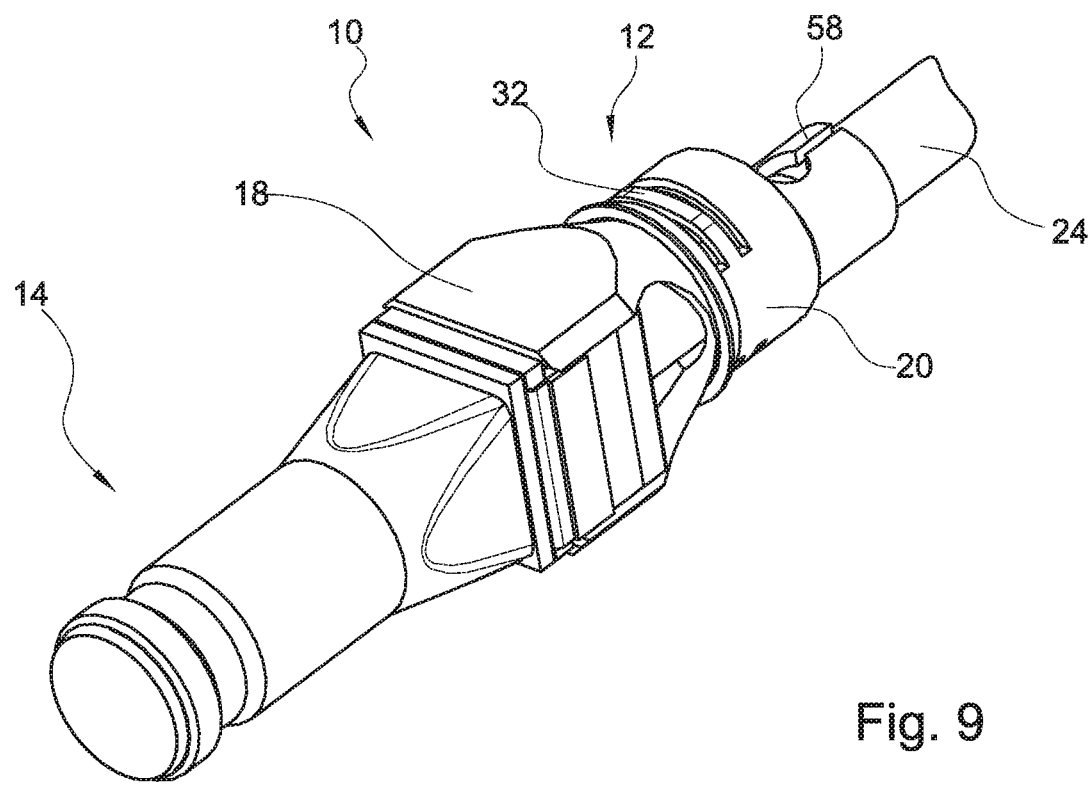
FIG. 9 shows a perspective view of the video endoscope shown in FIG. 8 with the metal shield removed.

FIG. 9 shows the video endoscope 10 in the perspective view of FIG. 8, wherein the metal shield 22 has been removed.

Figure 10:
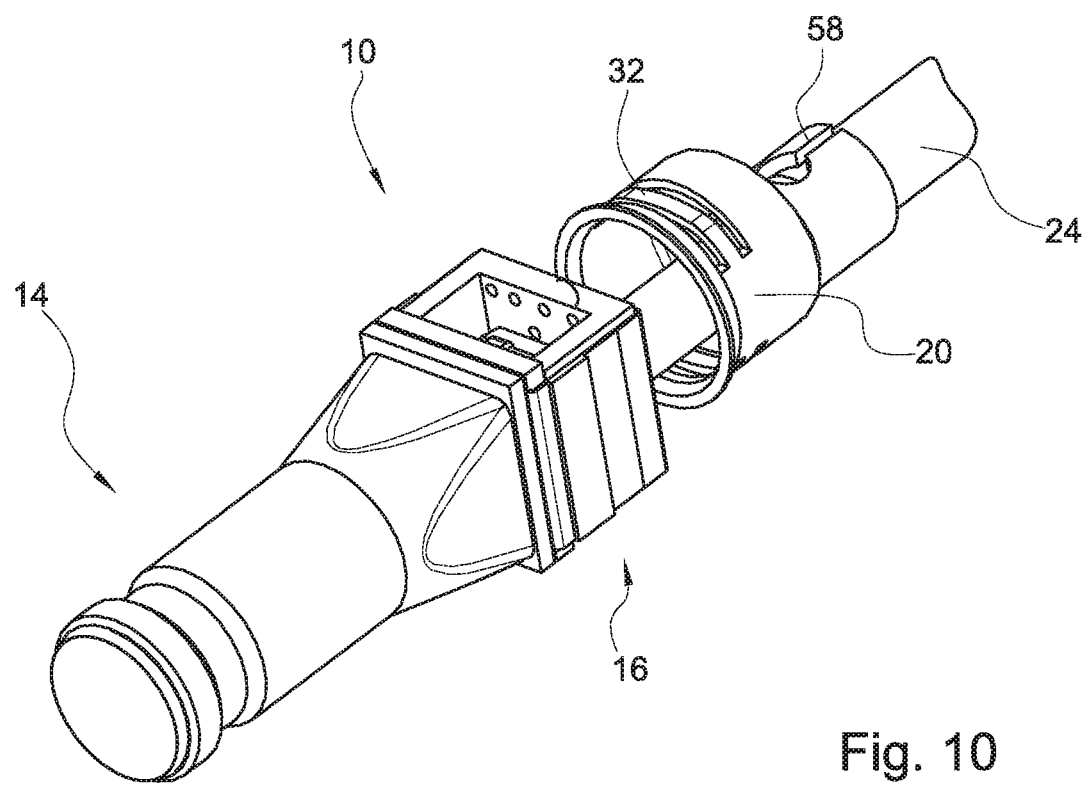
FIG. 10 shows a perspective view of the video endoscope shown in FIG. 9 with the video module holder removed.

FIG. 10 shows the video endoscope 10 in the perspective view of FIG. 9, wherein the video module holder 18 has been removed.

What is claimed is:

1. Video endoscope comprising a distal end with a video camera assembly and a lens assembly arranged along a longitudinal axis, the video camera assembly comprising a video module, a video module holder, a proximal bushing arranged on and adjacent to the video module holder, a metal shield enclosing the video module along the longitudinal axis, and a flexible video cable, wherein the video cable is connected to the video module, runs through the video module holder and the proximal bushing away from the video module and is in contact with the bushing, wherein the video module com-prises a video imager and control circuitry, wherein the metal shield has on its outside a dielectric coating obtained by material treatment of the metal shield, and wherein a maximum cross section of the distal end is less than 0.75 cm$^2$.

2. Video endoscope of claim 1, wherein the material treatment comprises or is constituted by one of oxidation, plasma electrolytic oxidation and micro arc oxidation.

3. Video endoscope of claim 1, wherein the metal shield is predominantly made of one of aluminum, magnesium and titanium.

4. Video endoscope of claim 1, wherein the metal shield is not covered by a heat-shrink tube.

5. Video endoscope of claim 1, wherein the metal shield is not covered by any plastic insulator.

6. Video endoscope of claim 1, wherein the metal shield has a first section with a first, at least substantially rectangular cross section, and a second section with a second, at least substantially oval cross section.

7. Video endoscope of claim 6, wherein the metal shield has an intermediate section that transitions the first cross section into the second cross section along the longitudinal axis.

8. Video endoscope of claim 1, wherein the metal shield has on its inside a contact area where the dielectric coating is not applied.

9. Video endoscope of claim 8, wherein the contact area is in electrical contact with the bushing.

10. Video endoscope of claim 1, wherein a largest cross section of the metal shield viewed perpendicular to the longitudinal axis has the shape of a square with rounded corners.

11. Video endoscope of claim 1, wherein the video cable has a conductive shield that is electrically connected to the bushing.

12. Video endoscope of claim 1, wherein the video cable has a conductive shield that is electrically connected to the bushing using a solidified conductive adhesive.

13. Video endoscope of claim 1, wherein the bushing has a clearance opening directed perpendicular to the longitudinal axis allowing to reach the video cable inside the bushing.

14. Video endoscope of claim 1, wherein the bushing has at its proximal end a fixing area where the bushing is in contact with the video cable, the fixing area comprising at least one slit that allows the fixing area to be compressed and to be pressed onto the video cable.

15. Video endoscope of claim 1, wherein the bushing has at its proximal end an opening with a center that is offset in a direction perpendicular to the longitudinal axis from a center of the video imager.

16. Video endoscope of claim 1, wherein the bushing has a deformable rib that deforms towards the inside of the bushing when pushed in a direction perpendicular to the longitudinal axis, wherein the video module holder has a recess at a position corresponding to the rib, so that the rib can be pushed at least partially into the recess thus fixing the bushing relative to the video module holder regarding at least one of a movement in a direction of the longitudinal axis and a rotation around the longitudinal axis.

17. Video endoscope of claim 1, wherein the bushing is made of a conductive material and/or the video module holder is made of a plastic material.

18. Video endoscope of claim 1, wherein the bushing is electrically connected to the metal shield by a solidified conductive adhesive.

19. Video endoscope of claim 1, wherein the flexible video cable runs completely through an entire length of at least the video module holder or the proximal bushing.

20. Video endoscopy system comprising a video endoscope according to claim 1 and further comprising a handle, a pull wire and a camera control unit, wherein a first end of the pull wire is attached to the distal end of the video endoscope and a second end of the pull wire is attached to a control element on the handle, so that by manipulating the control element a user can adjust a deflection of the distal end, and wherein the video cable is connected to the camera control unit.

* * * * *